US00PP19110P2

(12) United States Plant Patent
van der Meer

(10) Patent No.: US PP19,110 P2
(45) Date of Patent: Aug. 19, 2008

(54) *CHRYSANTHEMUM* PLANT NAMED 'BECORO'

(50) Latin Name: *Chrysanthemum×morifolium*
Varietal Denomination: Becoro

(75) Inventor: Adrianus L. M. van der Meer, Monster (NL)

(73) Assignee: Beckenkamp Plants B.V., Maasdijk (NL)

( * ) Notice: Subject to any disclaimer, the term of this patent is extended or adjusted under 35 U.S.C. 154(b) by 0 days.

(21) Appl. No.: 11/705,871

(22) Filed: Feb. 14, 2007

(51) Int. Cl.
*A01H 5/00* (2006.01)

(52) U.S. Cl. ..... Plt./286

(58) Field of Classification Search ..... Plt./286
See application file for complete search history.

*Primary Examiner*—Kent L. Bell
*Assistant Examiner*—June Hwu
(74) *Attorney, Agent, or Firm*—C. A. Whealy

(57) ABSTRACT

A new and distinct cultivar of *Chrysanthemum* plant named 'Becoro', characterized by its compact, upright and uniformly mounded plant habit; dark green-colored foliage; uniform flowering response; early flowering habit, freely flowering habit; semi-double-type inflorescences with red purple and white bi-colored ray florets; and good postproduction longevity with plants maintaining good substance and color for about three weeks in an interior environment.

1 Drawing Sheet

Botanical designation: *Chrysanthemum×morifolium.*
Cultivar denomination: 'Becoro'.

BACKGROUND OF THE INVENTION

The present invention relates to a new and distinct cultivar of *Chrysanthemum* plant, botanically known as *Chrysanthemum×morifolium,* commercially grown as a potted *Chrysanthemum* and hereinafter referred to by the name 'Becoro'.

The objective of the breeding program is to create new potted *Chrysanthemum* cultivars with uniform plant growth habit, desirable inflorescence form and floret colors.

The new *Chrysanthemum* originated from an open-pollination in April, 2002, in Monster, The Netherlands of an unnamed selection of *Chrysanthemum×morifolium,* not patented, as the female, or seed, parent with an unknown selection of *Chrysanthemum×morifolium,* as the male, or pollen, parent. The new *Chrysanthemum* was discovered and selected by the Inventor as a single flowering plant within the progeny of the stated open-pollination in a controlled environment in Monster, The Netherlands in October, 2002.

Asexual reproduction of the new *Chrysanthemum* by vegetative tip cuttings was first conducted in Monster, The Netherlands in October, 2002. Asexual reproduction by cuttings has shown that the unique features of this new *Chrysanthemum* are stable and reproduced true to type in successive generations.

SUMMARY OF THE INVENTION

Plants of the cultivar Becoro have not been observed under all possible environmental conditions. The phenotype may vary somewhat with variations in environment such as temperature, daylength and light intensity, without, however, any variance in genotype.

The following traits have been repeatedly observed and are determined to be the unique characteristics of 'Becoro'.

These characteristics in combination distinguish 'Becoro' as a new and distinct potted *Chrysanthemum* cultivar:

1. Compact, upright and uniformly mounded plant habit.
2. Dark green-colored foliage.
3. Uniform flowering response.
4. Early flowering habit, eight-week response time.
5. Freely flowering habit.
6. Semi-double-type inflorescences with red purple and white bi-colored ray florets.
7. Good postproduction longevity with plants maintaining good substance and color for about three weeks in an interior environment.

Plants of the new *Chrysanthemum* differ from plants of the female parent selection primarily in ray floret coloration as plants of the female parent selection have red purple-colored ray florets.

Plants of the new *Chrysanthemum* can be compared to plants of the *Chrysanthemum* cultivar Kilargo, not patented. In side-by-side comparisons conducted in Monster, The Netherlands, plants of the new *Chrysanthemum* differed from plants of the cultivar Kilargo in the following characteristics:

1. Plants of the new *Chrysanthemum* and the cultivar Kilargo differed slightly in leaf coloration.
2. Inflorescences of plants of the new *Chrysanthemum* were flatter than inflorescences of plants of the cultivar Kilargo.
3. Inflorescences of plants of the new *Chrysanthemum* and the cultivar Kilargo differed in ray floret coloration as plants of the cultivar Kilargo had red purple-colored ray florets.

BRIEF DESCRIPTION OF THE PHOTOGRAPHS

The accompanying photographs illustrate the overall appearance of the new *Chrysanthemum.* These photographs show the colors as true as it is reasonably possible to obtain in colored reproductions of this type. Colors in the photographs may differ slightly from the color values cited in the detailed botanical description which accurately describe the colors of the new *Chrysanthemum.*

The photograph at the top of the sheet comprises a side perspective view of typical flowering plant of 'Becoro'.

The photograph at the bottom of the sheet is a closeup view of the low (left) and upper (right) surfaces of typical inflorescences and leaves of 'Becoro'.

DETAILED BOTANICAL DESCRIPTION

The aforementioned photographs and following observations and measurements describe plants grown during the spring in Monster, The Netherlands during the summer in a glass-covered greenhouse and under conditions and practices which approximate those generally used in commercial potted *Chrysanthemum* production. During the production of the plants, day temperatures ranged from 17.5° C. to 30° C., night temperatures ranging from 18.5° C. to 24° C. and light levels averaging 5 kilolux. Plants were grown under photoinductive short day/long night treatments. Plants used in the photographs and for the description were not pinched and were about nine months from planting. In the following description, color references are made to The Royal Horticultural Society Colour Chart, 2001 Edition, except where general terms of ordinary dictionary significance are used.

Botanical classification: *Chrysanthemum×morifolium* cultivar Becoro.

Parentage:

*Female, or seed, parent.*—Unnamed selection of *Chrysanthemum×morifolium,* not patented.

*Male, or pollen, parent.*—Unknown selection of *Chrysanthemum×morifolium,* not patented.

Propagation:

*Type.*—Terminal vegetative cuttings.

*Time to initiate roots, summer.*—About six days at temperatures of about 20° C.

*Time to initiate roots, winter.*—About seven days at temperatures of about 20° C.

*Time to produce a rooted young plant, summer.*—About 14 days at temperatures of about 20° C.

*Time to produce a rooted young plant, winter.*—About 16 days at temperatures of about 20° C.

*Root description.*—Fine; light brown in color.

*Rooting habit.*—Freely branching; moderately dense.

Plant description:

*Appearance.*—Herbaceous compact semi-double-type potted *Chrysanthemum.* Stems upright and outwardly spreading giving a uniformly mounded appearance to the plant. Moderately vigorous growth habit.

*Plant height.*—About 10 cm.

*Plant width.*—About 10 cm.

*Lateral branches.*—Length: About 3 cm to 8 cm. Diameter: About 4 mm. Strength: Strong. Texture: Pubescent. Color: Close to 146A to 146B.

Foliage description:

*Arrangement.*—Alternate, simple.

*Length.*—About 3.5 cm to 5.5 cm.

*Width.*—About 3 cm to 5.5 cm.

*Apex.*—Rounded to mucronate.

*Base.*—Attenuate.

*Margin.*—Palmately lobed, sinuses between lateral lobes mostly divergent.

*Texture, upper and lower surfaces.*—Rough, leathery with fine pubescence; veins prominent on lower surface.

*Color.*—Developing and fully expanded foliage, upper surface: Close to 137A; venation, 148B. Developing and fully expanded foliage, lower surface: Close to 147B; venation, 146B.

*Petiole length.*—About 5 mm to 1.2 cm.

*Petiole diameter.*—About 2.5 mm.

*Petiole color.*—Close to 146B to 146C.

Inflorescence description:

*Appearance.*—Semi-double-type inflorescence form with elliptic-shaped ray florets. Inflorescences borne on terminals above foliage. Disk and ray florets arranged acropetally on a capitulum. Inflorescence not fragrant.

*Flowering response.*—Under natural conditions, plants flower in the autumn/winter in the Northern Hemisphere. At other times of the year, inflorescence initiation and development can be induced under short day/long night conditions (at least 13.5 hours of darkness). Early flowering habit; plants flower about eight weeks later.

*Postproduction longevity.*—Inflorescences maintain good color and substance for about three weeks in an interior environment.

*Quantity of inflorescences.*—Freely flowering, about 25 inflorescences develop per plant.

*Inflorescence bud.*—Height: About 4 mm. Diameter: About 6 mm. Shape: Oblate. Color: Close to 146B.

*Inflorescence size.*—Diameter: About 2 cm to 4 cm. Depth (height): About 1 cm to 2 cm. Diameter of disc: About 1 cm.

*Ray florets.*—Shape: Elliptic. Orientation: Initially upright, then about 90° from vertical or perpendicular to peduncle. Aspect: Initially incurved, then mostly flat. Length: About 1 cm to 1.5 cm. Width: About 5 mm to 7 mm. Apex: Rounded to emarginate. Base: Attenuate; short corolla tube. Margin: Entire. Texture, upper and lower surfaces: Smooth, glabrous, satiny. Number of ray florets per inflorescence: About 30 to 40 arranged in two to three whorls. Color: When opening, upper surface: Close to 70B; towards the margins, close to 155D. When opening, lower surface: Close to 69D. Fully opened, upper surface: Close to 70A to 70B; towards the margins, close to 155D; central color becoming closer to 70B with development. Fully opened, lower surface: Close to 69D; towards the center, underlain with 70B.

*Disc florets.*—Arrangement: Massed at center of receptacle. Shape: Tubular, elongated. Apex: Five-pointed. Length: About 4 mm to 5 mm. Width: About 1 mm. Number of disc florets per inflorescence: About 120. Color, immature: Towards the base, close to 145D; towards the apex, close to 154B. Color, mature: Towards the base, close to 145C; towards the apex, close to 9C.

*Phyllaries.*—Number of phyllaries per inflorescence: About 16. Length: About 3 mm. Width: About 1.5 mm. Shape: Lanceolate. Apex: Acute. Base: Truncate. Texture, upper surface: Smooth, waxy. Texture, lower surface: Pubescent. Color, upper surface: Close to 146A. Color, lower surface: Close to 147A.

*Peduncles.*—Length: First peduncle: About 2.5 cm. Fourth peduncle: About 3.5 cm. Diameter (first peduncle): About 1.5 mm. Angle: About 30° from vertical. Strength: Strong, flexible. Texture: Pubescent. Color: Close to 137B.

*Reproductive organs.*—Androecium: None observed. Gynoecium: Present on both ray and disc florets. Stigma shape: Bi-parted. Stigma length: About 1 mm. Stigma diameter: About 0.3 mm. Stigma color: Close to 145C to 145D.

*Seed/fruit.*—Seed and fruit production has not been observed.

Disease/pest resistance: Resistance to pathogens and pests common to *Chrysanthemums* has not been observed on plants grown under commercial conditions.

Temperature tolerance: Plants of the new *Chrysanthemum* have demonstrated good tolerance to low temperatures of about 5° C. and high temperatures of about 30° C.

What is claimed

1. A new and distinct *Chrysanthemum* plant named 'Becoro' as illustrated and described.

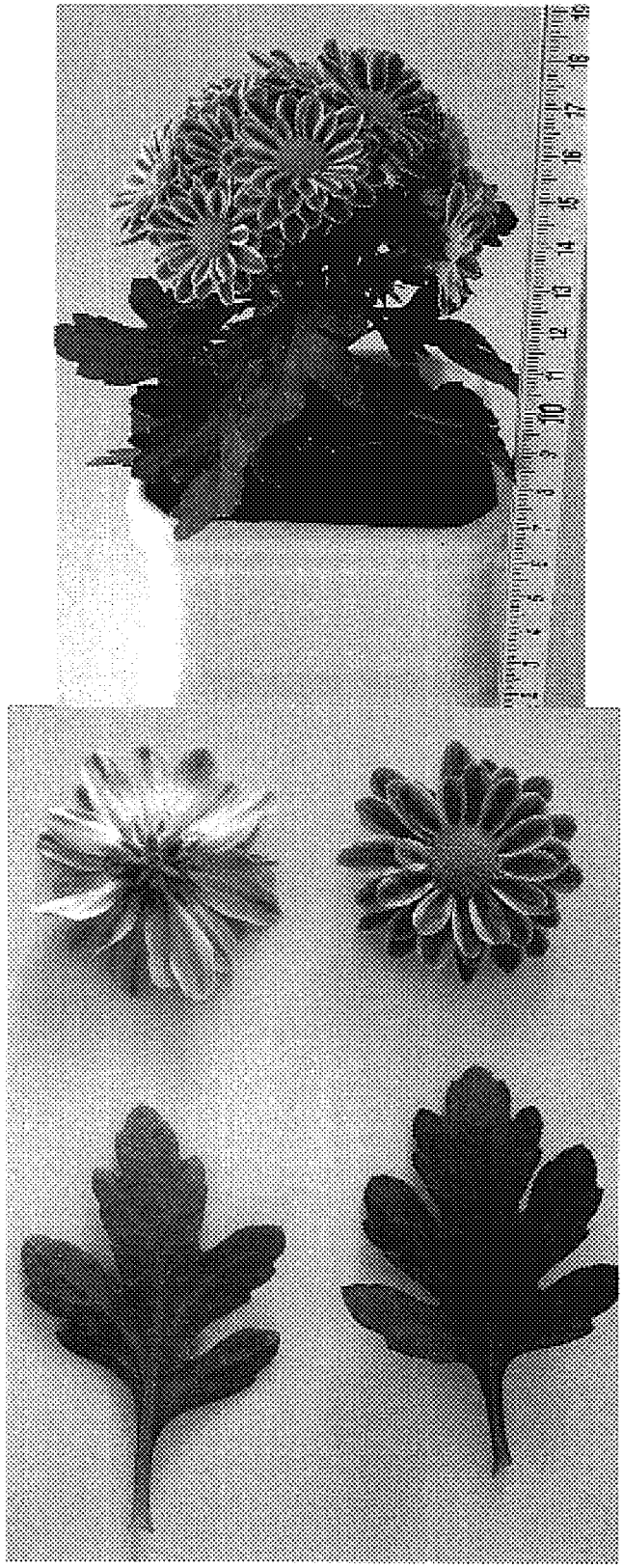

* * * * *